United States Patent
Zhou et al.

(10) Patent No.: US 10,118,964 B2
(45) Date of Patent: *Nov. 6, 2018

(54) CONSTRUCTION AND APPLICATION OF BISPECIFIC ANTIBODY HER2XCD3

(71) Applicant: Wuhan YZY Biopharma Co., Ltd., Wuhan (CN)

(72) Inventors: Pengfei Zhou, Wuhan (CN); Jing Zhang, Wuhan (CN); Lingli Hu, Wuhan (CN); Rui Wang, Wuhan (CN); Xiang Zhou, Wuhan (CN); Kesu Fan, Wuhan (CN)

(73) Assignee: Wuhan YZY Biopharma Co., Ltd., Wuhan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/449,656

(22) Filed: Mar. 3, 2017

(65) Prior Publication Data

US 2017/0174765 A1 Jun. 22, 2017

Related U.S. Application Data

(63) Continuation of application No. 14/803,278, filed on Jul. 20, 2015, now Pat. No. 9,611,325.

(30) Foreign Application Priority Data

Jan. 21, 2015 (CN) .......................... 2015 1 0029954

(51) Int. Cl.
*C07K 16/28* (2006.01)
*C07K 16/46* (2006.01)
*C07K 16/32* (2006.01)
*A61K 39/00* (2006.01)

(52) U.S. Cl.
CPC ...... *C07K 16/2809* (2013.01); *C07K 16/2878* (2013.01); *C07K 16/2887* (2013.01); *C07K 16/2896* (2013.01); *C07K 16/32* (2013.01); *C07K 16/468* (2013.01); *A61K 2039/505* (2013.01); *C07K 2317/31* (2013.01); *C07K 2317/51* (2013.01); *C07K 2317/515* (2013.01); *C07K 2317/60* (2013.01); *C07K 2317/622* (2013.01); *C07K 2317/92* (2013.01); *C07K 2317/94* (2013.01)

(58) Field of Classification Search
CPC .............. C07K 16/468; C07K 2317/31; C07K 2317/622
See application file for complete search history.

(56) References Cited

U.S. PATENT DOCUMENTS

| 9,079,965 B2 | 7/2015 | Zhou et al. |
| 9,562,110 B2 * | 2/2017 | Zhou ................... C07K 16/32 |
| 9,611,325 B2 * | 4/2017 | Zhou ................. C07K 16/2809 |
| 9,777,073 B2 * | 10/2017 | Zhou ..................... C07K 16/468 |
| 2007/0123479 A1 | 5/2007 | Kufer et al. |
| 2014/0154253 A1 | 6/2014 | Ng et al. |
| 2015/0284475 A1 | 10/2015 | Zhou et al. |
| 2016/0090426 A1 | 3/2016 | Zhou et al. |

FOREIGN PATENT DOCUMENTS

| CN | 104558192 | 4/2015 |
| JP | 3587881 | 11/2004 |
| WO | WO-2014-079000 | 5/2014 |

OTHER PUBLICATIONS

Ahmad et al., "ScFv Antibody: Principles and clinical application", Clinical and Developmental Immunology, pp. 1-15, (2012).
Artufel et al., "Molecular Protocol for Her-2/neu analysis in breast carcinoma." Cl in Transl Oncol, 2005,7(11):504-511.
Carter et al., "HER-2/neu over-expression induces endothelial cell retraction." Int Cancer, 2001, 91(3):295-299.
Goueli et al., "Upregulation of the Catalytic Telomerase Subunit by the Transcription Factor ER81 and Oncogenic HER2/Neu, Ras, or Raf." Molecular and Cellular Biology, 24:1:25-35 (Jan. 2004).
Hynes et al., "The biology of erbB-2/neu/HER-2 and its role in cancer," Journal of Biochem. Biophys Acta 1198:165-184, 1994.
Kranz et al., Partial elucidation of an anti-hapten repertoire in BALB/c mice: comparative characterization of several monoclonal antifluorescyl antibodies. Mol Immunol. 18(10) :889-898 (1981).
Michaelson et al., "Anti-tumor activity of stability-engineered IgG-like bispecific antibodies targeting Trail-R2 and LTbetaR", mAbs 1:2:128-141, 2009.
Shih et al., "Transforming genes of carcinomas and neuroblastomas introduced into mouse fibroblasts." Nature, 290(5803):261-264. (1981).
Signoretti et al., "Her-2-neu expression and progression toward androgen independence in human prostate cancer", Journal of the National Cancer Institute, vol. 92, pp. 1918-1925 (2000).
Slamon, "Human breast cancer: correlation of relapse and survival with amplification of the HER-2/neu oncogene." Science. 1987 (235):177-182.
The Freedom(TM) Cho-S(TM) Kit User Guide, Thermo Fisher Scientific, Publication No. MAN0003505, 2015.
Verri et al., HER2/neu oncoprotein overexpression in epithelial ovarian cancer: evaluation of its prevalence and prognostic significance. Oncology, 68(2-3):154-161 (2005).

* cited by examiner

*Primary Examiner* — Jessica H Roark
(74) *Attorney, Agent, or Firm* — Sheppard Mullin Richter & Hampton LLP

(57) ABSTRACT

The present invention provides a bispecific antibody. The bispecific antibody provided by the present invention comprises a single-chain unit and a monovalent unit, wherein the single-chain unit has a specific binding capability against a surface antigen CD3 of an immune cell; the monovalent unit has a specific binding capability against a surface antigen HER2 of a tumor cell; the single-chain unit comprises a single-chain variable fragment ScFv fused with an Fc fragment; and the monovalent unit comprises a light chain and heavy chain pair. The present invention also provides a preparation method of the bispecific antibody and pharmaceutical use of these antibodies.

6 Claims, 6 Drawing Sheets

Specification includes a Sequence Listing.

CONSTRUCTION AND APPLICATION OF BISPECIFIC ANTIBODY HER2XCD3

This application is a continuation of U.S. patent application Ser. No. 14/803,278, filed Jul. 20, 2015, which claims priority to and benefits of Chinese Patent Application No. CN 201510029954.X, filed Jan. 21, 2015 and of International Application No. PCT/CN2014/082590, filed Jul. 21, 2014, the entire disclosures of which are hereby incorporated by reference.

TECHNICAL FIELD

The present invention relates to the technical field of immunology, in particular to construction and a preparation method of a bispecific antibody.

BACKGROUND ART

The bispecific antibody (BiAb) is an artificial antibody containing two specific antigen binding sites and can build a bridge between a target cell and a functional molecule (cell) to generate an oriented effector function. The BiAb has a broad application prospect in the biomedicine, especially in immunotherapy of tumors. To kill tumor cells through the BiAb-mediated cytotoxic effect is a hotspot of current application research of immunotherapy, and its principal characteristic lies in that the BiAb can simultaneously bind to a tumor-associated antigen and a target molecule on an immunologic effector cell and directly trigger the specific killing effect of the immunologic effector cell on the tumor cell. Immune cell antigens and tumor cell antigens under study and some background arts of related technology development will be introduced below.

1. CD3

The CD3 module consists of four subunits δ, ε, γ and ζ of which the molecular masses are 18.9 kDa, 23.1 kDa, 20.5 kDa and 18.7 kDa respectively and which have 171, 207, 182 and 164 amino acid residues in the length direction respectively. All the subunits constitute six peptide chains which tightly bind to a T cell receptor (TCR) usually to form a TCR-CD3 complex containing eight peptide chains (as shown in structural schematic diagram 1). This complex has the functions of transducing a T cell activation signal and stabilizing a TCR structure. The cytoplasmic domain of CD3 contains an immunoreceptor tyrosine-based activation motif (ITAM), and the TCR identifies and binds to an antigen peptide presented by an MHC (major histo-compatibility complex) molecule, resulting in that a tyrosine residue in a conserved sequence of the ITAM of CD3 is phosphorylated by tyrosine protein kinase p56lck in a T cell and then other tyrosine protein kinases (such as ZAP-70) containing an SH2 (Ser homology 2) structural domain can be collected. The phosphorylation of ITAM and the binding to ZAP-70 are one of important biochemical reactions in the early stage of the T cell activation signal transduction process. Therefore, the CD3 molecule has the function of transducing the activation signal generated when the TCR recognizes antigens.

2. HER2

Shih, et al. in 1981 (Shih C, Padhy L C, Murray M, et al. Transforming genes of carcinomas and neuroblastomas introduced into mouse fibroblasts [J]. Nature, 1981, 290 (5803):261-264.) cloned oncogene neu from mouse neuroblastoma genomes for the first time, and Slamon, et al. (1987, Science 2; 35; 177-182) separated the HER2 gene from a human cDNA library. It was found in the following sequence analysis and chromosome spectrum analysis that neu and HER2 are of the same gene which is customarily called as a HER2/neu gene or c-erbB-2 gene. HER2 is the 2rd member in the human epidermal growth factor receptor family belonging to the type 1 receptor tyrosine kinase family (also known as the ErbB receptor family) and takes an important regulating effect in growth, differentiation and metastasis processes of many normal and abnormal epidermic cells, and incidence, development and illness state of many tumors are closely related to the activity of HER2. There are a total of four receptors, namely HER1, HER2, HER2 and HER4 in the family. These receptors may interact to generate a heterogenetic or homologous dimer and activate multiple signal transduction pathways in cells, wherein the HER2 plays an important role in the signal transduction process of cells. The HER2 structurally comprises a binding domain of extracellular growth factors, a lipophilic transmembrane domain and an intracellular domain with regulatory carboxyl terminal fragments. The intracellular domain of the HER2 receptor has protein tyrosine kinase (PTK) activity and also possesses a number of tyrosine reside Tyr phosphorylation sites itself. The specific growth factor can induce the dimerization and stimulate the cross phosphorylation of the receptor after binding to the HER2 receptor, and the phosphorylated receptor can transduce an extracellular growth signal into the nucleus rapidly, and stimulate and control cell division-related genetic expression.

The HER2 which is positioned in human chromosome 17q21 and encodes a transmembrane protein having the molecular weight being 185 kD has the tyrosine kinase RTK activity, is at an inactive state under a normal condition, participates in regulation of normal differentiation of cells, is generally expressed only in the fetus state and is only weakly expressed in a very few of normal tissues in an adult stage. The HER2 gene in the normal cell is a two-copy gene and can be activated through gene mutation, and its amplification will cause transcription up-regulation and protein synthesis increase, thus inhibiting tumor cell apoptosis, accelerating tumor cell proliferation, up-regulating vascular enodthelial growth factor VEGF/vascular permeability factor VPF, accelerating tumor angiogenesis, increasing invasive ability of tumor cells and destroying anti-invasion barriers of body tissues, etc [Artufel M V, Valero A C, Llado R R, et al. Molecular Protocol for Her-2/neu analysis in breast carcinoma [J]. Clin Transl 0ncol, 2005, 7. (11):504-511.]. The overexpression of the HER2 protein also plays an important role in inducing division, proliferation and transformation of cells and accelerating metastasis, invasion and adhesion of tumors [Hynes N E, Stem D F. The biology of erB-2/Neu/HER-2 and its role in cancer [J]. Biochem Biophys AcTa, 1994, 1198 (2-3):165-184.].

Except for gene mutation or amplification, up-regulation of the HER2 expression may activate two main signal transduction pathways, namely an MAPK pathway and a PI3K/Akt pathway at the downstream of HER2, thus giving rise to a waterfall type chain reaction, regulating apoptosis-related genes, accelerating infinite proliferation and differentiation of cells, inhibiting apoptosis and further generating cancerization. The former pathway mainly participates in mitosis of cells and the latter pathway mainly affects survival and apoptosis of cells. The HER2 can activate the Ets transcription factor family member ER81 through the MAPK pathway to up-regulate human telomerase terminal transferase reverse transcriptase hTERT, which further cause abnormal activation of the telomerase terminal transferase of cells, so that the cells are transformed to enter a permanent proliferation state. [Goueli B S, Janknecht R. Upregulation of the catalytic telomerase subunit by the transcription factor ER81 and oncogenic HER2/Neu, Ras, or Raf. Mol Cell Biol. 2004, 24:25-35.]. After being activated, PI3K can catalyze phosphatidyl inositol PI to generate PIP2 and PIP3 which are important second messengers in a cell and can activate downstream protein kinase Akt/PKB to further cause phosphorylation of downstream BAD protein, thus preventing BAD and apoptosis proteins Bcl-2 and Bcl-XL from constituting a complex and simultaneously inducing the phosphorylation of forkhead transcription factors 1 to further inhibit the expression of apoptosis protogene.

Moreover, the HER2 oncogene is also a tumor metastasis driving factor, and the overexpression of the HER2 can increase the tumor cell metastasis capability through starting multiple metastasis-related mechanisms, such as cell migration rate, in vitro invasiveness and W-type collagenase activity and also can influence synthesis of certain adhesion molecules, such as epithelial cell E-cadherin, thereby accelerating metastasis. Carter, et al (Carter W, Hoying J, Boswell C, et al. HER-2/neu over-expression induces endothelial cell retraction [J]. Int Cancer, 2001, 91(3): 295-299), under study, considered that the over-expression of HER2 can induce endothelial cell retraction and dilated intercellular space, and it is easy for tumor cells to pass through among endothelial cells to generate shift of metastasis. Most studies considered that the HER2 gene amplification and/or protein over-expression were/was often a cue for us that the tumor malignancy is high and the metastasis ability is strong.

The over-expression of HER2 is often related to occurrence of tumors, for example:

(1) Gastric cancer: the gastric cancer is one of the most common malignant tumors in China, its prognosis is poor, the five-year survival rate of the gastric cancer in the development period is 5-20% only and the median survival time thereof does not exceed on year. The over-expression rate variation of the HER2 protein in the gastric cancer is detected, by different research groups, to be 7-43%. Positive expression of the HER2 protein in the gastric cancer is related to the tumor differentiation degree, Lauren typing and WHO typing and is not related to age, gender tumorigenesis portion and clinical stages.

(2) Breast cancer: researches indicated that the HER2 generated gene amplification and protein over-expression in 20-30% of primary breast infiltrating ductal carcinoma. High expression of the HER2 always causes malignant metastasis of cells, and therefore, the HER2-positive breast cancer has strong infiltrability, short disease free survival time and poor prognosis. In vitro experiments displayed that apoptosis of tumor cells can be caused by inhibiting the expression of HER2.

(3) Ovarian cancer: the ovarian cancer is a main reason for gynecological tumor death. The over-expression of HER2 in the ovarian cancer is similar to that in the breast cancer, which accounts for 15-30%. Studies of Verri, et al (Verri, E, Guglielmini P, Puntoni M, et al. HER2/neu oncoprotein overexpression in epithelial ovarian cancer: evaluation of its prevalence and prognostic significance [J]. Oncology, 2005, 68:154-161.) indicated that the total survival time of an HER2-positive (2+/3+) patient was remarkably shortened compared with that of an HER2-negative patient (0/1+) (29 months vs 48 months, P<0.05). The over-expression of the HER2 was found respectively through observing 20 cell lines from ovary in III and IV ovarian cancers.

(4) Prostate cancer: the genesis of the prostate cancer is androgen-dependent, and tumors will be retracted after medicinal or surgical castration, but will be finally changed to be androgen-independent to continuously grow, which is the most primary problem in the current treatment of the prostate cancer. Studies indicated that the HER2 is a main mediator of the prostate cancer in the process of transforming from androgen dependence to androgen independence. Signoretti, et al (Signoretti S, Montironi R, Manola J, et al. Her-2-neu expression and progression toward androgen independence in human prostate cancer [J]. J Natl Cancer Inst, 2000, 92: 1918-1925.), under study, analyzed the expression levels of DNA, RNA and protein of tumor samples in different clinical stages, and the result displayed that over-expressed HER2 existed in 25% of patient (UNT tumor) whose prostate cancers were removed through surgery, 59% of patients (TAA tumor) who accepted antiandrogen therapy before surgery and 78% of patients (androgen-independency AI) who failed androgen therapy and generated osseous metastasis.

(5) Lung cancer: the over-expression of HER2 in the lung cancer is mainly related to genetic transcription and postranscriptionaly modification. Domestic researches indicated that the over-expression of HER2 mainly happened in the non-small cell lung cancer, mainly in glandular cancer rather than squamous cancer. However, the detection result from 88 hungarian patients suffering the non-small cell lung cancer indicated that the over-expression of HER2 only existed in five cases all of which suffer squamous-cell carcinoma, resulting in different research results. Furthermore, there are different conclusions in the relationship between the over-expression of HER2 in the lunch cancer and the cell differentiation degree.

An antibody drug trastuzumab, specific to HER2 targets, has the trade name Herceptin and is a humanized monoclonal antibody taking HER2 as a target. Herceptin® (trastuzumab) is obtained by mosaicism of a stable domain of non-specific human IgG and an antigenic determinant of mouse anti-HER2 protein IgG through a genetic engineering method, not only has high affinity to an HER2 receptor, but also solves the problem that a mouse-derived antibody is applied to immunogenicity of the human body and can reduce the generation of human anti-mouse antibodies, thus avoiding from being removed by a reticuloendothelial system. In vivo and in vitro experiment researches indicated that the application of Herceptin® (trastuzumab) to down-regulation of expression was capable of retarding the cell growth and remarkably improving its sensitivity to chemoradiotherapy. In 1998, the US Federal Drug Administration (FDA) approved this drug was used for second-line or third-line therapy of HER2 over-expressed metastatic breast cancer, which was also the first and the only humanized monoclonal antibody drug approved for treating HER2/neu protein expressed positive metastatic breast cancer and early-stage breast cancer.

3. Technological Development of Bispecific Antibody

The bispecific antibody is an antibody in which two antigen binding sites in one antibody molecule can bind to two different epitopes respectively.

The antibody drug refers to a biomacromolecular drug prepared by an antibody engineering technology taking a cell engineering technology and a genetic engineering technology as main bodies and has the advantages of high specificity, uniform property, capability of realizing direction preparation against specific targets, etc. The monoclonal antibody is mainly applied to the following three aspects in clinical practice: oncotherapy, therapy of immune diseases and anti-infective therapy. Wherein, the oncotherapy is the most extensive field for monoclonal antibody application at present, and products for oncotherapy in monoclonal antibody products that have entered clinical trial and listed in the market account for about 50%. The oncotherapy by monoclonal antibodies is an immunotherapy for killing target cells by stimulating the immune system against specific targets of pathological cells, in order to enhance the effector function of the antibody, and especially the effect of killing tumor cells; and as concerned in multiple methods that have been tried by people to transform antibody molecules, the bispecific antibody has been one of the development trends for improving the antibody therapy effect and has become the hotspot in the field of antibody engineering researches.

The bispecific antibody for immunotherapy is an artificial antibody containing two kinds of specific antigen binding sites, is capable of building a bridge between the target cell and the functional molecule (cell) and stimulating oriented immunoreaction and has a wide application prospect in immunotherapy of tumors.

4. Preparation of Bispecific Antibody

The bispecific antibody can be obtained by multiple paths, and its preparation methods mainly include a chemical coupling method, a hybrid-hybridoma technique and a genetically engineered antibody preparation method. As concerned in the chemical coupling method, two different monoclonal antibodies are connected together in a chemical coupling manner to prepare a bispecific monoclonal antibody, which is the earliest bispecific monoclonal antibody concept. As concerned in the hybrid-hybridoma technique, the bispecific monoclonal antibody is produced by a cell hybridization method or a ternary hybridoma manner, and these cell hybridomas or ternary hybridomas are obtained through fusion of built hybridomas, or the fusion of the built hybridomas and mouse-derived lymphocytes and could only produce a mouse-derived bispecific antibody, and are thus limited to a great extent in application. With the rapid development of the molecular biological technology, multiple construction modes of humanized bispecific antibodies in genetic engineering have arisen, which are mainly classified into four categories, namely a bispecific micro-antibody, a double-chain antibody, a single-chain bivalent antibody and a multivalent bispecific antibody. At present, there have been several international genetically engineered bispecific antibody drugs that have been entered the clinical trial stage with a better application prospect.

5. Adoptive Immunotherapy of Tumors

As concerned in the adoptive immunotherapy of tumors, mainly comprising immunotherapy of LAK cells, TIL cells, activated T lymphocyte and CIK cells, autologous or allogeneic immunocompetent cells are delivered into the body of a patient after in vitro amplification to directly kill tumor cells, and regulate and enhance the immune function of the organism. However, the immunotherapy can be only used to remove a small number of scattered tumor cells, has a very limited effect on end-stage solid tumors, and is thus usually used as an adjuvant therapy to be combined with conventional methods, such as surgery, chemotherapy and radiotherapy. After a large number of tumor cells are cleared up by the conventional methods, residual tumor cells are removed by the immunotherapy, so that the comprehensive therapy effect on tumors can be improved. Wherein, as a new method for comprehensive therapy of tumors, the adoptive immunotherapy has been widely matched with conventional surgery, radiotherapy, chemotherapy and other cell and molecule therapies and holds great promise in therapy of multiple tumors. However, it should be a more ideal method that one end of the bispecific antibody can bind to a surface antigen CD3 of a cultured immune cell and is delivered into the body along with it, and the other end of the bispecific antibody can well bind to the surface antigen of the tumor cell; and therefore, the bispecific antibody can build a bridge between the tumor cell and the immune cell in the body, so that the immune cells are gathered around the tumor cells to further kill the tumor cells. By this method, the metastasis and diffusion of the tumor cells can be effectively solved, and the defects, such as 'halfway, easy metastasis and large side effect' in the three traditional therapy modes, namely surgery, radiotherapy and chemotherapy are overcome.

SUMMARY OF THE INVENTION

Terms and Abbreviations

BiAb: bispecific antibody
TA: tumor antigen
VH: heavy chain variable region
VL: light chain variable region
CL: constant region of light chain
CDR: Complementarity determining regions (CDRs)
ScFv: single-chain variable fragment
CLD: cell line development
FACS: fluorescence-activated cell sorting As concerned in the present invention, the construction of the new molecule—the bispecific antibody is implemented through genetic engineering and antibody engineering methods against the shortcomings of the conventional monoclonal antibodies, the T cell-mediated immunotherapy is increased for the traditional monoclonal antibodies on the basis of killing the tumor cells mainly by means of CDC, ADCC and apoptosis ability, and thus the effect of killing the tumor cells by the immune system is greatly improved.

Concretely, the present invention provides the following technical solutions: in one embodiment, a bispecific antibody is provided, which is characterized in that it comprises: (a) a monovalent unit which is a light chain-heavy chain pair having a specific binding capability to surface antigens of the tumor cells, preferably HER2, CD20, CD30 and CD133, more preferably HER2; and (b) a single-chain unit which is a fusion peptide comprising a single-chain variable fragment ScFv and an Fc fragment having a hinge region, a CH2 structural domain and a CH3 structural domain, wherein the immune cell directed to the fusion peptide is selected from a T cell, an NKT cell or a CIK cell; and preferably, the fusion peptide has a specific binding capability to the surface antigen CD3 of the immune cell.

In one embodiment, the CH2 structural domain of the single-chain unit of the bispecific antibody is positioned between the ScFv fragment and the CH3 structural domain; and the single-chain unit does not contain a CH1 structural domain.

In one embodiment, the single-chain variable fragment of the bispecific antibody consists of a light chain variable region structural domain and a heavy chain variable structural domain, both of which are targeted to the antigen epitope CD3.

In one embodiment, in the monovalent unit, both a light-chain constant region structural domain and a light-chain variable region structural domain of a light chain are targeted to the tumor antigen epitope HER2; both a heavy-chain constant structural domain CH1 and a heavy-chain variable structural domain of a heavy chain are targeted to the tumor antigen epitope HER2; the light chain binds to the heavy chain through a disulfide bond; and the heavy chain binds to the fusion peptide through one or more disulfide bonds, and preferably, said one or more disulfide bonds are formed among amino acid residues of the hinge region between a CH1 (or VLs) structural domain and a CH2 structural domain.

In one embodiment, the single-chain unit comprises an anti-CD3 antibody directed to CD3, wherein the monovalent unit comprises an anti-HER2 antibody directed to HER2.

In one embodiment, the amino acid sequence of a heavy chain of the anti-HER2 antibody is the amino acid sequence as shown in SEQ ID NO: 1, the amino acid sequence of a light chain of the anti-HER2 antibody is the amino acid sequence as shown in SEQ ID NO: 3 and the amino acid sequence of the ScFv-Fc of the anti-CD3 antibody is the amino acid sequence as shown in SEQ ID NO: 5; in addition, cysteine of the heavy chain of the anti-HER2 antibody on the site 223 is connected with cysteine of the light chain of the anti-HER2 antibody on the site 214 in a manner of disulfide bonds, cysteines of the heavy chain of the anti-HER2 antibody on sites 229 and 232 are connected with cysteines of the ScFv-Fc of the anti-CD3 antibody on sites 255 and 258 respectively in a manner of disulfide bonds, the sites 395 and 412 in the heavy chain of the anti-HER2 antibody are in salt bridge connection with sites 428 and 397 of the ScFv-Fv of the anti-CD3 antibody, and the site 369 in the heavy chain of the anti-HER2 antibody is in hump-indent-cavity connection with the site 436 of the ScFv-Fc of the anti-CD3 antibody.

In one embodiment, the heavy chain in the monovalent unit contains a human or humanized Fc fragment, preferably, the Fc fragment of the heavy chain comprises a human IgG Fc fragment; and an Fc fragment of the fusion peptide contains a human or humanized Fc fragment, preferably the Fc fragment of the fusion peptide comprises a human IgG Fc fragment.

In one embodiment, both the human IgG Fc fragment of the monovalent unit and the IgG Fc fragment of the single-chain unit are connected through a salt bridge and a hump-indent-cavity structure.

In one embodiment, a preparation method of a bispecific antibody is provided, comprising:

(1) establishing a heavy chain and a light chain of the monovalent unit to a first expression vector respectively and establishing a single-chain unit to a second expression vector;

(2) co-transfecting the first expression vector and the second expression vector to a cell, culturing and taking supernatant; and (3) separating the expression supernatant to obtain a purified bispecific antibody; preferably, said cell is a CHO-S cell; or preferably, the separation step comprises: capturing all antibodies with Fc structural domains from the expression supernatant through a protein A affinity column, separating the target bispecific antibody from byproducts through SP cation-exchange chromatography, then passing a Q column and finally concentrating and displacing a buffer solution PBS.

In one embodiment, the first expression vector is pCHO1.0; and the second expression vector is pCHO1.0-hygromycin.

In one embodiment, the monovalent unit is an anti-HER2 antibody, primers used for amplifying the light chain of the anti-HER2 antibody are Kozak(EcoRV)F, MK-leader (EcoRV)F and hIgK (PAcI)R, and the Kozak sequence, the MK-leader and the restriction enzyme cutting sites EcoRV and PacI are introduced to the light chain through overlap PCR amplification; primers used for amplifying the heavy chain of the anti-HER2 antibody are Kozak(AvrII)F, MK-leader (AvrII)F and HIgGI(BstZ17I)R, and the Kozak sequence, the MK-leader and restriction enzyme cutting sites AvrII and BstZ17I are introduced to the heavy chain; the amplified LCgene fragment is subject to homologous recombination with the pCHO1.0 expression vector suffering restriction enzyme cutting via EcoRV and PacI to obtain an anti-HER2 light chain-loaded expression vector and is then subject to homologous recombination with HC after suffering restriction enzyme cutting via AvrII and BstZ17I to obtain an anti-HER2 pCHO1.0 expression vector of which the plasmid is named as pCHO1.0-anti-HER2-HL-KKW.

The single-chain unit is an anti-CD3 ScFv-Fv antibody, primers used for amplifying said antibody are Kozak(AvrII) F, MK-leader (AvrII)F, L2K-VH(MK)F1 and hIgG1 (BstZ17I)R, and the anti-CD3 ScFv-Fc-loaded expression vector of which the plasmid is named as pCHO1.0-hygromycin-L2K-ScFv-Fc-LDY is obtained through implementing overlap PCR amplification of an anti-CD3 ScFv-Fc structural domain, introducing the Kozak sequence, the MK-leader and restriction enzyme cutting sites AvrII and BstZ17I into ScFv-Fc and carrying out homologous recombination of on the amplified gene fragment and the pCHO1.0 expression vector suffering restriction enzyme cutting, the anti-CD3ScFv-Fc-loaded expression vector of which the plasmid is named as pCHO1.0-hygromycin-L2K-ScF-Fc-LDY is obtained.

In one embodiment, as concerned in any one bispecific antibody or use of the bispecific antibody prepared via any one of methods forementioned in preparing drugs, said drugs are used to treat tumor or related diseases caused by HER2 specific antigen expression or kill cells expressing HER2.

In one embodiment, as concerned in any one bispecific antibody or use of the bispecific antibody prepared via any one of methods forementioned in preparing drugs, said drugs are used to screen drugs for treating tumor cell-associated diseases caused by expression of the HER2 specific antigen from a tumor cell line or evaluate the efficacy of drugs for treating tumor cell-associated diseases caused by expression of the HER2 specific antigen. The present invention also provides the following technical solution:

The present invention provides a novel antibody called as the bispecific antibody and establishes a method for carrying out immunotherapy by using an immune system of the human body and performing the pharmacological study of the bispecific antibody. As a novel antibody for a pharmacological mode, this bispecific antibody introduces the specific cytotoxicity efficacy of the T cell to tumor antigens, such as HER2.

The present invention provides a new method for preparing the bispecific antibody MSBODY (monomer and ScFv-Fc bispecific antibody) as shown in FIG. 2. The bispecific antibody comprises two groups of heavy and light chain combinations, wherein one group specifically binds to one kind of antigen, is subject to some transformations on its heavy chain Fc region, and is thus not easy to form a dimer per se relative to a wild type; whereas, the other group specifically binds to another kind of antigen, is subject to some other transformations on its heavy chain Fc region and is thus also not easy to form a dimer per se, and moreover, a hybrid dimer is easy to form between the two groups of heavy and light chains. In addition, the antibody structure of one of the two groups is a monovalent unit and the other group is a single chain (ScFv-Fc), so that the possibility that respective light chain and the heavy chain of the opposite side are mismatched is avoided, and thus a bispecific antibody protein molecule of 125 KD is formed. After Fc transformation, the heavy chain and the single chain of the monovalent unit are naturally iso-dimerized, and meanwhile, CL and CH1 are naturally dimerized to finally form the MSBODY, wherein the arrangement sequence of various structural domains and the structural schematic diagram of the MSBODY are as shown in FIG. 2.

According to the method for preparing the bispecific antibody as disclosed in the present invention, the bispecific antibody is prepared. Wherein, the bispecific antibody taking HER2 and CD3 as targets is named as HER2×CD3, and as shown in FIG. 2, the anti-HER2 side is of a monovalent unit form and comprises an anti-HER2 heavy chain and the light chain, and the anti-CD3 side is of a ScFv-Fc form and comprises anti-CD3VH, VL and Fc structural domains. The bispecific antibody forementioned is established through an antibody genetic engineering method and involves a monovalent unit heavy chain and monovalent unit light chain double-promoter expression vector and an ScFv-Fc expression vector. Primers are designed according to the monovalent unit light chain (LC), the monovalent unit heavy chain (HC), ScFV, Fc gene sequence and multiple cloning sites in the vectors. Wherein, PCR amplification is implemented respectively for LC, HC, ScFv and Fc, and a gene fragment is obtained via PCR or overlap extension by PCR and is then cloned via a homologous recombination method. The pCHO1.0 or pCHO1.0-hygromycin vector is subject to restriction enzyme cutting and then a PCR product and vectors suffering restriction enzyme cutting are purified and recovered, the LC fragment and the HC fragment are cloned onto the pCHO1.0 vector in a homologous recombination manner by two steps, and the ScFv-Fc fragment is cloned onto the pCHO1.0-hygromycin vector in a homologous recombination manner and is then sequenced. According to the expression and detection of the recombinant protein MSBODY in mammalian cells, plasmids expressing a heavy chain and a light chain of the monovalent unit and plasmids expressing the single-chain unit are co-transfected to the mammalian cells by using a transfection reagent, and then supernatant is collected and undergoes, SDS-PAGE and western blotting, to detect the expression condition of the MSBODY. The supernatant of the culture solution subject to transfection expression is centrifuged and filtered, is then diluted with a binding buffer solution, passes through an affinity column, is eluted with an elution buffer solution, and is subject to SDS-PAGE detection to purify the protein.

The technical solution of the present invention has the beneficial effects:

1. The present application provides a heterodimer antibody comprising two different antigen-binding polypeptide units. The heterodimer and its corresponding homodimer are different in molecular weight and can be distinguished according to the molecular weight, and therefore, the purity of the bispecific antibody can be determined more conveniently. One of the two antigen-binding polypeptide units comprises a light chain-heavy chain pair similarly to a wild type antibody and is also called as a 'monovalent unit' in the whole present application. The other antigen-binding polypeptide unit comprises a single-chain variable fragment (ScFv). So, the ScFv can be fused to a constant fragment (Fc) of the antibody. The fusion peptide in the full text of the present application is also called as a 'single-chain unit'.

2. The present invention discloses establishment and its application of a novel bispecific antibody MSBODY-mediated immune cell-killing in vitro and vivo pharmalogical experiment method. The present invention includes preparation of an immune cell-killing bispecific antibody mediated in the bispecific antibody drug research process, as well as establishment and detection of a bispecific antibody in vitro and vivo pharmacological model. The bispecific antibody MOBODY comprises a group of single-chain unit (a ScFv-binding Fc combination), and the other group of monovalent unit (a heavy and light chain combination), wherein the monovalent unit specifically binds to a kind of human tumor cell antigens comprising a series of tumor cell membrane surface antigens, such as HER2, and is subject of some transformations in its heavy chain Fc region, and is thus not easy to form a dimer per se relative to the wild type; whereas, the other group of single-chain unit specifically binds to another kind of human T cell antigen CD3, is subject to some transformations in its heavy chain Fc region as well, and is thus also not easy to form a dimer per se, and moreover, a heterodimer is easy to form between the two groups of units. In the meantime, the bispecific antibody can build a bridge between the target cell and the functional molecule (cell) to stimulate the oriented immunoreaction. In the presence of of immune cells, the bispecific antibody as disclosed in the present invention has an extremely strong killing effect on tumor cells and thus has a wide application prospect in immunotherapy of tumors.

What is surprising, the present application has proved that this unsymmetrical antibody is stable and has high antigen binding efficiency, which is unexpected since it has been proved that even the homodimer of the single-chain antibody is instable under the physiological condition. For instance, 'ScFv Antibody: Principles and Clinical Application,' (Clinical and Developmental Immunology, 2012: 980250(2012)) of Ahmad, et al, indicated that ScFv-based IgG antibodies are instable and need to be further transformed so as to reduce the aggregation and improve the stability.

In addition, because of having asymmetry, the heterodimer has isoelectric points different from those of the homodimer consisting of any one antigen-binding polypeptide unit. Based on the isoelectric point difference between the heterodimer and the homodimer, the required heterodimer and homodimer can be separated easily, and thus the difficulty in downstream technique development generally existing in the bispecific antibodies is greatly reduced.

BRIEF DESCRIPTION OF THE DRAWINGS

Drawings that need to be used in the example will be briefly introduced below in order to illustrate the technical solution in the example of the present application more clearly, and it is apparent for those common skilled in the art that the drawings described as below are just some example recorded in the present invention and other drawings can also be acquired on the basis of those drawings on the premise of not paying creative work, wherein.

SPECIFIC MODES FOR CARRYING OUT THE INVENTION

Figure 1:
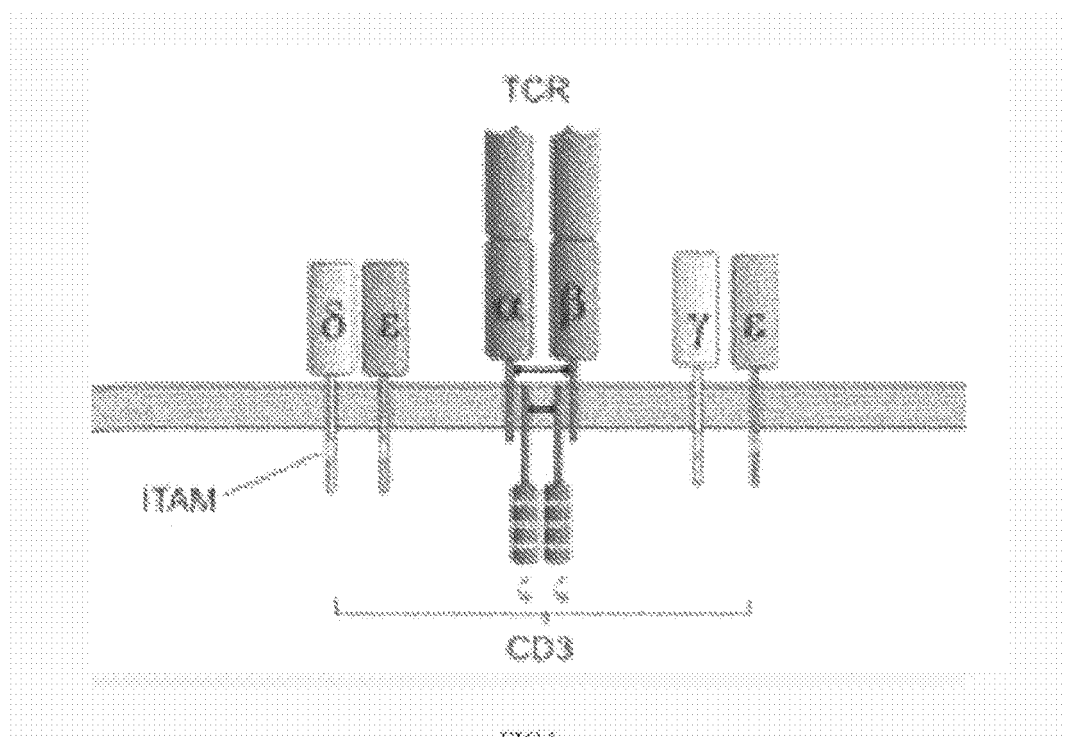
FIG. 1 is a structural schematic diagram of the CD3 molecule.
Figure 2:
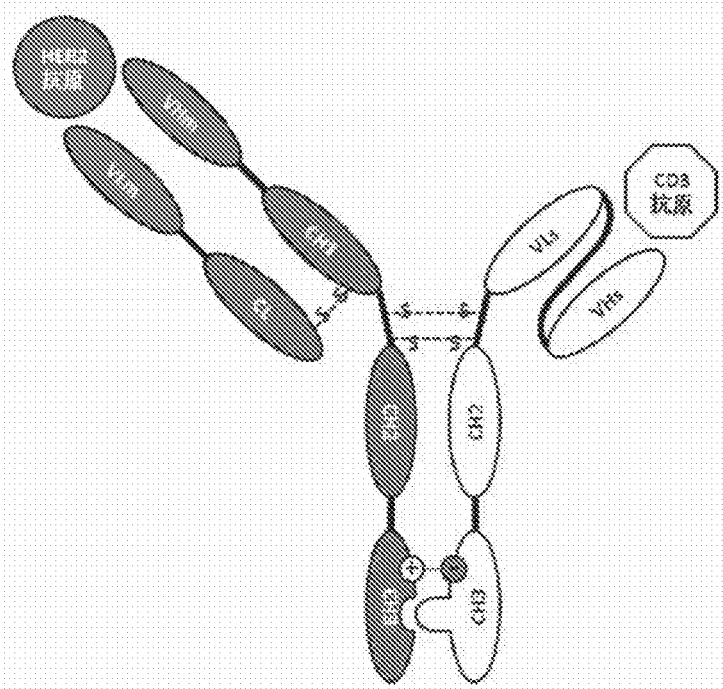
FIG. 2 is a schematic diagram of the HER2×CD3 bispecific antibody molecule.

Example 1: Construction of Expression Vector of Bispecific Antibody (HER2×CD3, M802)

1. Sequence Design of Bispecific Antibody

The bispecific antibody taking HER2 and CD3 as targets is named as HER2×CD3 MSBODY, wherein the monovalent unit is an anti-HER2 heavy chain and light chain pair, and the amino acid sequence of its variable region refers to a sequence (a PDB database No. 1N8Z) of a monoclonal antibody Herceptin® (trastuzumab) and comprises anti-HER2 heavy chain and light chain and contains Fab and FC structural domains; the single-chain unit is of an anti-CD3 ScFv-Fc form, the amino acid sequence of its variable region refers to a sequence (refer to SEQ ID NO: 2 of US20070123479) of a monoclonal antibody L2K and comprises anti-CD3 VH, VL and Fc structural domains. Wherein, both the heavy chain Fc of the monovalent unit and the heavy chain Fc of the single-chain unit (the same as the heavy chain Fc of human IgG1) are subject to amino acid mutation (the specific mutation process refers to PCT/CN2012/084982), and are thus not easy to form a homodimer respectively, but easy to form a heterodimer, namely the bispecific antibody HER2×CD3MSBODY M802. In the meantime, in order to ensure that M802 can be expressed in a CHO (Cricetulusgriseus, hamster, Chinese, ovary) cell and secreted into a culture medium, the leading peptide sequence of a mouse-derived antibody kappa chain is selected as a secretory signal peptide. The amino acid sequences and the nucleotide sequences of various structural domains and signal peptide refer to the following SEQ ID NO: 1-8. The signal peptide directly binds to the terminal N of the antibody variable region. In the patent PCT/CN2012/084982, the variable region of the monovalent unit of the anti-HER2×CD3 MSBODY is from Herceptin® (trastuzumab), and the variable region of the single-chain unit is from humanized OKT3. The MSBODY as number M801 in the present invention is taken as a reference antibody.

Heavy Chain Amino Acid Sequence (Herceptin® (trastuzumab), SEQ ID NO. 1) of the Monovalent Unit
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLWCLVKGFYPSDIAVEWESNGQPEN

NYDTTPPVLDSDGSFFLYSDLTVDKSRWQQGNVFSCSVMHEALHNHYTQ

KSLSLSPGK-

Heavy Chain Nucleotide Sequence (Herceptin® (trastuzumab), SEQ ID NO. 2) of the Monovalent unit
GAAGTGCAGCTGGTGGAAAGCGGCGGCGGCCTGGTGCAGCCGGGCGGAT

CCCTGCGCCTGAGCTGCGCGGCGAGCGGCTTTAACATTAAAGATACCTA

TATTCATTGGGTGCGCCAGGCGCCGGGCAAAGGCCTGGAATGGGTGGCG

CGCATTTATCCGACCAACGGCTATACCCGCTATGCGGATAGCGTGAAAG

GCCGCTTTACCATTAGCGCGGATACCAGCAAAAACACCGCGTATCTGCA

GATGAACAGCCTGCGCGCGGAAGATACCGCGGTGTATTATTGCAGCCGC

TGGGGCGGCGATGGCTTTTATGCGATGGATTATTGGGGCCAGGGCACCC

TGGTGACCGTGAGCTCAGCCTCCACCAAGGGCCCATCGGTCTTCCCCCT

GGCACCCTCCTCCAAGAGCACCTCTGGGGGCACAGCGGCCCTGGGCTGC

CTGGTCAAGGACTACTTCCCCGAACCGGTGACGGTGTCGTGGAACTCAG

GCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTG

GGCACCCAGACCTACATCTGCAACGTGAATCACAAGCCCAGCAACACCA

AGGTGGACAAGAAAGTTGAGCCCAAATCTTGTGACAAAACTCACACATG

CCCACCGTGCCCAGCACCTGAACTCCTGGGGGGACCGTCAGTCTTCCTC

TTCCCCCCAAAACCCAAGGACACCCTCATGATCTCCCGGACCCCTGAGG

TCACATGCGTGGTGGTGGACGTGAGCCACGAAGACCCTGAGGTCAAGTT

CAACTGGTACGTGGACGGCGTGGAGGTGCATAATGCCAAGACAAAGCCG

CGGGAGGAGCAGTACAACAGCACGTACCGTGTGGTCAGCGTCCTCACCG

TCCTGCACCAGGACTGGCTGAATGGCAAGGAGTACAAGTGCAAGGTCTC

CAACAAAGCCCTCCCAGCCCCCATCGAGAAAACCATCTCCAAAGCCAAA

-continued
GGGCAGCCCCGAGAACCACAGGTGTACACCCTGCCCCCATCCCGGGATG

AGCTGACCAAGAACCAGGTCAGCCTGTGGTGCCTGGTCAAAGGCTTCTA

TCCCAGCGACATCGCCGTGGAGTGGGAGAGCAATGGGCAGCCGGAGAAC

AACTACGATACCACGCCTCCCGTGCTGGACTCCGACGGCTCCTTCTTCC

TCTACAGCGATCTCACCGTGGACAAGAGCAGGTGGCAGCAGGGGAACGT

CTTCTCATGCTCCGTGATGCATGAGGCTCTGCACAACCACTACACGCAG

AAGAGCCTCTCCCTGTCTCCGGGTAAATGA

Light Chain Amino Acid Sequence (Herceptin®
(trastuzumab), (SEQ ID NO. 3) of the Monovalent
Unit
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIKRTVAAPSVFIFPPSDEQLKSGTASVVCLLNNFYPREAKVQ

WKVDNALQSGNSQESVTEQDSKDSTSLSSTLTLSKADYEKHKVYACEVT

HQGLSSPVTKSFNRGEC-

Light Chain Nucleotide Sequence (Herceptin®
(trastuzumab), (SEQ ID NO. 4) of the Monovalent
Unit
GATATTCAGATGACCCAGAGCCCGTCAAGCTTAAGCGCGAGCGTGGGCG

ATCGCGTGACCATTACCTGCCGCGCGAGCCAGGATGTGAACACCGCGGT

GGCGTGGTATCAGCAGAAACCGGGCAAAGCGCCGAAACTGCTGATTTAT

AGCGCGAGCTTTCTGTATAGCGGCGTGCCGAGCCGCTTTAGCGGCAGCC

GCAGCGGCACCGATTTTACCCTGACCATTAGCAGCCTGCAGCCGGAAGA

TTTTGCGACCTATTATTGCCAGCAGCATTATACCACCCCGCCGACCTTT

GGCCAGGGTACCAAAGTGGAAATTAAACGAACTGTGGCTGCACCATCTG

TCTTCATCTTCCCGCCATCTGATGAGCAGTTGAAATCTGGAACTGCCTC

TGTTGTGTGCCTGCTGAATAACTTCTATCCCAGAGAGGCCAAAGTACAG

TGGAAGGTGGATAACGCCCTCCAATCGGGTAACTCCCAGGAGAGTGTCA

CAGAGCAGGACAGCAAGGACAGCACCTACAGCCTCAGCAGCACCCTGAC

GCTGAGCAAAGCAGACTACGAGAAACACAAAGTCTACGCCTGCGAAGTC

ACCCATCAGGGCCTGAGCTCGCCCGTCACAAAGAGCTTCAACAGGGGAG

AGTGTTAG

Single-Chain Amino Acid Sequence (L2K, (SEQ ID
NO. 5) of the Single-Chain Unit
DIKLQQSGAELARPGASVKMSCKTSGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSSGGGGSGGGGSGGGGSDIQLTQSPAIMSA

SPGEKVTMTCRASSSVSYMNWYQQKSGTSPKRWIYDTSKVASGVPYRFS

GSGSGTSYSLTISSMEAEDAATYYCQQWSSNPLTFGAGTKLELKGAAAE

PKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQV

SLTCRVKGFYPSDIAVEWESNGQPENNYKTTPPVLKSDGSFFLASKLTV

DKSRWQQGNVFSCSVMHEALHNHYTQKSLSLSPGK-

Single-Chain Nucleotide Sequence (L2K, SEQ ID
NO. 6) of the Single-Chain Unit
GACATCAAACTGCAGCAGTCAGGGGCTGAACTGGCAAGACCTGGGGCCT

CAGTGAAGATGTCCTGCAAGACTTCTGGCTACACCTTTACTAGGTACAC

GATGCACTGGGTAAAACAGAGGCCTGGACAGGGTCTGGAATGGATTGGA

TACATTAATCCTAGCCGTGGTTATACTAATTACAATCAGAAGTTCAAGG

ACAAGGCCACATTGACTACAGACAAATCCTCCAGCACAGCCTACATGCA

ACTGAGCAGCCTGACATCTGAGGACTCTGCAGTCTATTACTGTGCAAGA

TATTATGATGATCATTACTGCCTTGACTACTGGGGCCAAGGCACCACTC

TCACAGTCTCCTCAGGAGGCGGCGGTTCAGGCGGAGGTGGAAGTGGTGG

AGGAGGTTCTGACATTCAGCTGACCCAGTCTCCAGCAATCATGTCTGCA

TCTCCAGGGGAGAAGGTCACCATGACCTGCAGAGCCAGTTCAAGTGTAA

GTTACATGAACTGGTACCAGCAGAAGTCAGGCACCTCCCCCAAAAGATG

GATTTATGACACATCCAAAGTGGCTTCTGGAGTCCCTTATCGCTTCAGT

GGCAGTGGGTCTGGGACCTCATACTCTCTCACAATCAGCAGCATGGAGG

CTGAAGATGCTGCCACTTATTACTGCCAACAGTGGAGTAGTAACCCGCT

CACGTTCGGTGCTGGGACCAAGCTGGAGCTGAAAGGTGCGGCCGCAGAG

CCCAAATCTTGTGACAAAACTCACACATGCCCACCGTGCCCAGCACCTG

AACTCCTGGGGGGACCGTCAGTCTTCCTCTTCCCCCCAAAACCCAAGGA

CACCCTCATGATCTCCCGGACCCCTGAGGTCACATGCGTGGTGGTGGAC

GTGAGCCACGAAGACCCTGAGGTCAAGTTCAACTGGTACGTGGACGGCG

TGGAGGTGCATAATGCCAAGACAAAGCCGCGGGAGGAGCAGTACAACAG

CACGTACCGTGTGGTCAGCGTCCTCACCGTCCTGCACCAGGACTGGCTG

AATGGCAAGGAGTACAAGTGCAAGGTCTCCAACAAAGCCCTCCCAGCCC

CCATCGAGAAAACCATCTCCAAAGCCAAAGGGCAGCCCCGAGAACCACA

GGTGTACACCCTGCCCCCATCCCGGGATGAGCTGACCAAGAACCAGGTC

AGCCTGACCTGCCTGGTCAAAGGCTTCTATCCCAGCGACATCGCCGTGG

AGTGGGAGAGCAATGGGCAGCCGGAGAACAACTACAAGACCACGCCTCC

CGTGCTGAAGTCCGACGGCTCCTTCTTCCTCGCCAGCAAGCTCACCGTG

GACAAGAGCAGGTGGCAGCAGGGGAACGTCTTCTCATGCTCCGTGATGC

ATGAGGCTCTGCACAACCACTACACGCAGAAGAGCCTCTCCCTGTCTCC

GGGTAAATGA

Leading Peptide Sequence (Amino Acid Sequence,
SEQ ID NO. 7) of Mouse-derived kappa Chain
METDTLLLWVLLLWVPGSTG Leading Peptide Sequence (Nucleotide Sequence,
SEQ ID NO. 8) of Mouse-derived kappa Chain
ATGGAGACAGACACACTCCTGCTATGGGTACTGCTGCTCTGGGTTCCAG

GTTCCACTGGT

2. Gene Cloning of Bispecific Antibody

Freedom® pCHO1.0 Expression Vector (short for pCHO1.0 purchased from a kit Freedom® CHO-S® Kit Article No. A13696-01 of Life technologies) was selected as an expression vector for cloning and expressing heavy chain and light chain genes of the monovalent unit, and a pCHO1.0-hygromycin expression vector was obtained by modification through replacing a puromycin gene in a pCHO1.0 vector with a hygromycin resistant gene and was selected to clone and express the single-chain unit. The primers in Table 1 were delivered to GENEWIZ, Inc, Suzhou for synthesis after being designed according to a cloning solution. The primers as shown in Table 1 were subject to PCR amplification, a gene plasmid obtained from gene synthesis or subcloned to pCDNA3.1 or pUC57 in the early-stage experiment acted as a template (which was descried in PCT/CN2012/084982 patent in detail), and then the heavy chain cDNA and the light chain cDNA of the monovalent unit were respectively established to the downstream of different promoters on the pCHO1.0 expression vector, and cDNA of the single-chain unit was established onto the pCHO1.0-hygromycin expression vector.

amplified LC gene fragment was subject to homologous recombination with a pCHO1.0 expression vector suffering restriction enzyme cutting via EcoRV and PacI to obtain the anti-HER2 light chain-loaded expression vector, and was then subject to homologous recombination with HC after suffering restriction enzyme cutting via AvrII and BstZ17I to obtain the anti-HER2 pCHO1.0 expression vector of which the plasmid is named as pCHO1.0-Herceptin-HL-KKW.

The anti-CD3ScFv-Fc-loaded expression vector of which the plasmid is named as pCHO1.0-hygromycin-L2K-ScFv-Fc-LDY was obtained through implementing overlap PCR amplification of an anti-CD3ScFv-Fc structural domain, introducing the Kozak sequence, MK-leader and restriction enzyme cutting sites AvrII and BstZ17I into ScFv-Fc and

TABLE 1

Primers Used in Gene Cloning of Bispecific Antibody

| Names of Fragments | Name of Primers | SEQ ID NO. | Sequences |
|---|---|---|---|
| Anti-HER2LC | Kozak(EcoRV)F | 1 | GAGGAAGGATCTCGAGCTCAAGCTTGATATCG CCGCCACCATG |
| | MK-leader(EcoRV)F | 2 | CAATTGATATCGCCGCCACCATGGAGACAGAC ACACTCCTGCTATGGGTACTGCTGCTC |
| | hIgK(PacI)R | 3 | CTTATCATGTCTGGATCGAAGCTTAATTAACT AACACTCTCCCCTGTTGAAG |
| Anti-HER2HC | Kozak(AvrII)F | 4 | CCCGAGGAGGAACGGTTCCGGGCCGCCTAGGG CCGCCACCATG |
| | MK-leader(AvrII)F | 5 | CAATTCCTAGGGCCGCCACCATGGAGACAGAC ACACTCCTGCTATGGGTACTGCTGCTC |
| | hIgG1(BstZ17I)R | 6 | CATAGAGTATAATATAGAGTATACACCTGCAG GTCATTTACCCGGAGACAGGGAG |
| Anti-CD3ScFv-Fc | Kozak(AvrII)F | 7 | CCCGAGGAGGAACGGTTCCGGGCCGCCTAGGG CCGCCACCATG |
| | MK-leader(AvrII)F | 8 | CAATTCCTAGGGCCGCCACCATGGAGACAGAC ACACTCCTGCTATGGGTACTGCTGCTC |
| | L2K-VH(MK)F1 | 9 | GCTATGGGTACTGCTGCTCTGGGTTCCAGGTT CCACTGGTGATATCAAACTGCAGCAGT |
| | hIgG1(BstZ17I)R | 10 | CATAGAGTATAATATAGAGTATACACCTGCAG GTCATTTACCCGGAGACAGGGAG |

Initial PCR amplification template DNA: 35 ng template DNA, such as a light chain and a heavy chain of a target antibody; 1 µl of 10 µM forward primer and reverse primer; 2.5 µl of 10×PCR Buffer solution; 1 µl of 10 mMdNTP; 1 µl of 2.5 unit/µl Pyrobest DNA polymerase (Takara, R005A); and distilled water to 25 µl by total volume, all of which are softly mixed in a 200 µL PCR tube and rapidly rotated in a microcentrifuge so as to collect the reaction mixture to the bottom of the tube. PCR reaction was performed by using Gene Amp PCR System 9700 (Applied Biosystem) according to the following settings: 5 minutes at 95° C.; and 25 cycles as below: 30 seconds each time at 95° C.; 30 seconds at 56° C.; and 1 minute at 72° C.

Via several cycles of overlap PCR amplification, the Kozak sequence, MK-leader and restriction enzyme cutting sites EcoRV and PacI were introduced into the light chain; and the Kozak sequence, the MK-leader and restriction enzyme cutting sites AvrII and BstZ17I were introduced into the heavy chain by the corresponding primers. Firstly, the carrying out homologous recombination on the amplified gene fragment and the pCHO1.0 expression vector suffering restriction enzyme cutting.

Example 2: Expression and Purification of Bispecific Antibody

1. Expression of Bispecific Antibody

Plasmid maxiprep was performed by using an endotoxin-free maxiprep kit (Qiagen, 12391) and specific operations were performed according to the instructions provided by the manufacturer. CHO-S cell culture was performed in a CDFortiCHO culture medium at 37° C. in a 5% $CO_2$ cell incubator according to the instructions provided by the manufacturer, and after the cells were prepared, plasmids pCHO1.0-Herceptin-HL-KKW and pCHO1.0-Herceptin-L2K-ScFv-Fc-LDY were co-transfected to the CHO-S cells by using a Maxcyte STX electroporation apparatus to express the anti-HER2×CD3 bispecific antibody M802 according to the instructions (Maxcyte) provided by the manufacturer. After culture for 14 days, expression supernatant was harvested by 800×g centrifugal.

2. Purification of Bispecific Antibody

Figure 3:
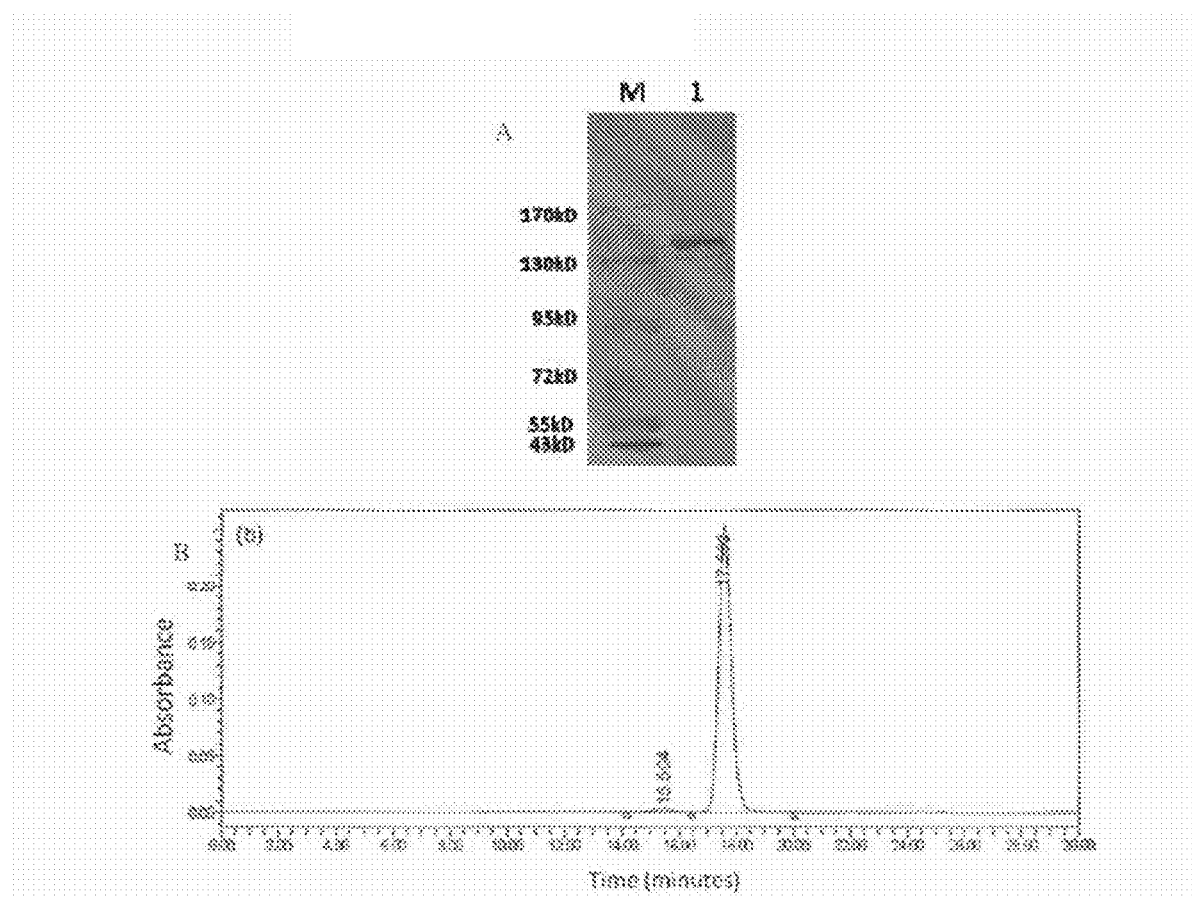
FIG. 3 is an electrophoresis and purity detection result diagram of the purified bispecific antibody, (A) non-reducing SDS-PAGE eletrophoresis; M: protein molecular weight marker; 1: M802; (B) HPLC-SEC purity peak shape diagram M802.

The expression supernatant was filtered with a 0.22 uM filter membrane, an antibody with an Fc structural domain was captured from the expression supernatant by using a MabselectSuRe affinity column (purchased from GE Company, Column Art. No. 18-1153-45 and Filler Art. No. 17-5438-01), passed through the affinity column which was balanced by using an equilibration buffer solution (50 mM $NaH_2PO_4$+40.5 mM $Na_2HPO_4$, pH7.0) and was eluted by using an elution buffer solution (50 mM citric acid+100 mM arginine, pH3.2). The target bispecific antibody and byproducts were separated by means of SP cation exchange chromatography, wherein the cation exchange column was purchased from GE Company (Column Art. No. 18-1153-44 and Filler Art. No. 17-1087-01); and after the column was balanced by using an equilibration buffer solution A (43.8 mM $NaH_2PO_4$+6.2 mM $Na_2HPO_4$, pH6.0), a sample was diluted with double pure water, was electrically conducted to a range from 3.0 ms to 3.5 ms and was subject to linear elution of 20 column volumes by using an elution buffer solution B (43.8 mM $NaH_2PO_4$+6.2 mM $Na_2HPO_4$+1M NaCl, pH6.0) after being combined with an SP column; and finally, Buffer PBS was concentrated and displaced. The purified bispecific antibody had the purity over 95% via SDS-PAGE and SEC detection (as shown in FIG. 3).

Example 3: Binding Activity Measurement (FACS) of Bispecific Antibody and Cells The bispecific antibody of the present invention binds to target antigens on the corresponding cells. As concerned in the present invention, with SK-BR-3 (purchased from China Center for Type Culture Collection) as an HER2 positive cell and Jurkat (American Type Culture Collection ATCC, TIB-152) as a CD3 positive cell, the cell binding activity therebetween was measured by means of the bispecific antibody prepared in the present invention.

Figure 4:
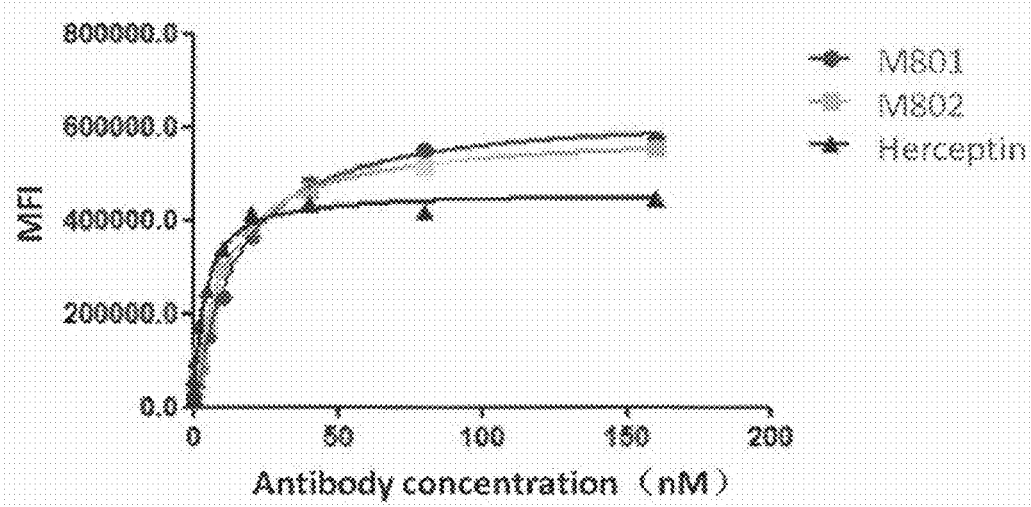
FIG. 4 is an affinity condition diagram of the HER2×CD3 bispecific antibody and the SK-BR-3 cell measured on the basis of fluorescence-activated cell sorting.

1. Detection of the Binding Activity of the Bispecific Antibody and the SK-BR-3 Cells Via Fluorescence-Activated Cell Sorting Enough SK-BR-3 cells were cultured, digested with 0.25% trypsin and collected by centrifugation. In the meantime, the bispecific antibody was diluted according to the concentration beginning from 160 nmol and four-fold gradient dilution to obtain six concentration gradients for later use. The collected cells were washed twice with PBS+1% FBS, the cells were resuspended to $4×10^6$ cell/ml with PBS+1% FBS and plated in a 96-well plate each well of which was loaded with 50 μl ($2×10^5$ cells), 50 μl of diluted bispecific antibody was added and cells were incubated for 1 hour at room temperature; and supernatant was removed by centrifugation, cells were washed twice with PBS, then resuspended with a diluted PE-marked anti-human IgG FC antibody (Biolegend, 409304), incubated for 30 minutes at room temperature in a dark place, washed twice with PBS, then resuspended with 100 μl PBS and detected on an instrument, and then, the binding affinity KD value of the bispecific antibody and KS-BR-3 was analyzed and calculated according to the mean fluorescence intensity by using software GraphPadPrism 5.0. The result displayed that the HER2×CD3 bispecific antibody had favorable binding activity with the HER2-positive SK-BR-3 cell (as shown in FIG. 4). The binding situation with the HER2-positive cell SK-BR-3 was illustrated as follows: the KD value of M801 was 14.84 nM, the KD value of M802 was 10.61 nM and the KD value of Herceptin® (trastuzumab) was 3.772 nM.

Figure 5:
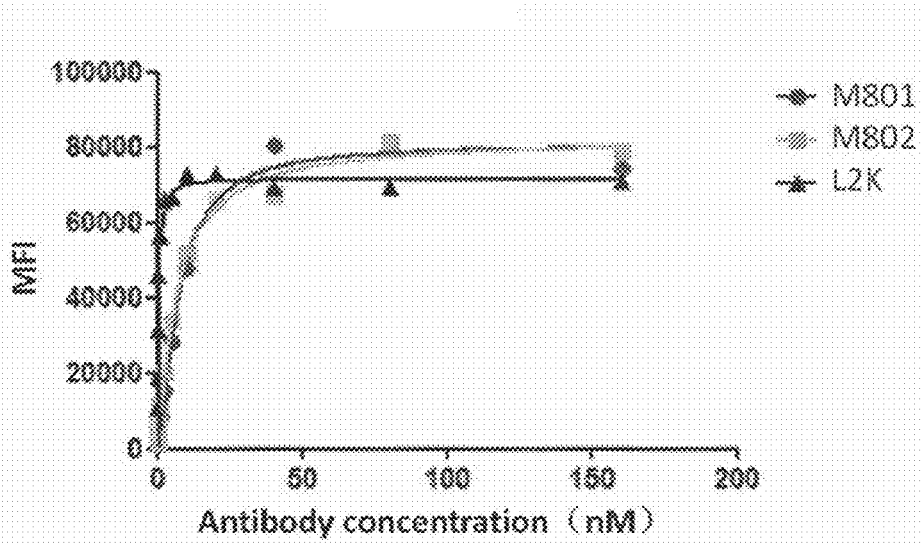
FIG. 5 is the affinity condition diagram of the HER2×CD3 bispecific antibody and the Jurkat cell measured based on fluorescence-activated cell sorting.

2. Detection of the Binding Activity of the Bispecific Antibody and Jurkat Cells Via Fluorescence-Activated Cell Sorting Enough Jurkat suspension cells were cultured and collected by centrifugation. The same as the steps described in the example forementioned, in the following experimental process, the cells resuspended with 100 μl PBS were detected on an instrument, and the binding affinity KD value of the bispecific antibody and the Jurkat cells was analyzed and calculated according to the man fluorescence intensity by using software GraphPadPrism 5.0. The result displayed that the HER2×CD3 bispecific antibody had favorable binding activity with the CD3-positive Jurkat cells (as shown in FIG. 5). The binding situation with the CD3-positive cells Jurkat was illustrated as follows: the KD value of M801 was 7.25 nM, the KD value of M802 was 6.61 nM and the KD value of Herceptin® (trastuzumab) was 0.39 nM.

Figure 6:
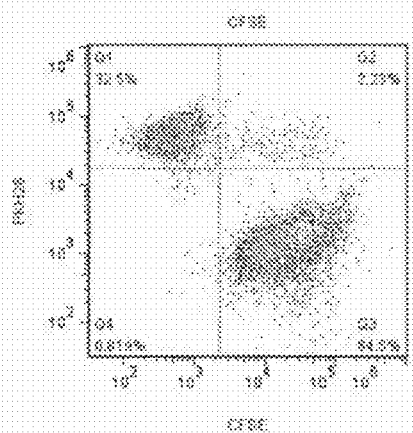
FIG. 6 is an antibody-free flow type scatter diagram of the HER2 positive cell NCI-N87 (CFSE stained) and the Jurkat cell (PKH26 stained).
Figure 7:
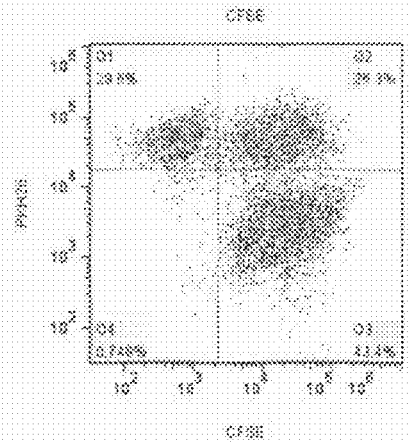
FIG. 7 is a co-incubation flow type scatter diagram of the HER2 positive cell NCI-N87 (CFSE stained) and the Jurkat cell (PKH26 stained) in the presence of M802.

3. Co-Binding Experiment of Bispecific Antibody-Mediated Immune Cells and Tumor Cells Cultured NCI-N87 (HER2-positive gastric cancer cells purchased from China Center for Type Culture Collection) and Jurkat cells were collected by centrifugation, washed twice with PBS and stained with CFSE and PKH-26 respectively. In the meantime, M802 was diluted to 160 nM. The stained NCI-N87 and Jurkat cells were centrifuged to remove supernatant, washed twice with PBS+1% FBS, and then resuspended to $4×10^6$ cell/ml with PBS+1% FBS respectively, cells were uniformly mixed according to a ratio of 1:1 and plated in a 96-well plate each well of which was loaded with 50 ul ($2×10^5$ cells), 50 ul of diluted bispecific antibody was added, and cells were incubated for 1 hour at room temperature; and supernatant was removed by centrifugation, the cells were washed twice with PBS and resuspended with 100 ul PBS finally, and the ratio of double positive cells was analyzed through detection on an instrument (FC500, Beckham) and was calculated by using software GraphPadPrism 5.0. The result displayed that in case of no M802, the ratio of bifluorescence via flow cytometer detection was very low (as shown in FIG. 6); under the condition of adding the HER2×CD3 bispecific antibody M802, the ratio of biofluorescence via flow cytometer detection reached 26.3%, which indicated that M802 could simultaneously bind to HER2-positive NCI-N87 cells and CD3-positive Jurkat cells and promote the co-binding of the two kinds of cells.

Example 4: Determination of Thermal Stability of Bispecific Antibody

1. Thermal Challenge Experiment of Bispecific Antibody

The antibody was diluted with PBS to 0.5 mg/mL, charged into PCR tubes according to a specification of 50 μL/tube and then subject to thermal treatment for 60 min on a PCR instrument (ABIPCR system 9700). The PCR instrument sets the temperature gradient from left to right and from 37° C. to 82° C., and each sample corresponds to one temperature. After treatment, the cooled samples were transferred into a 96-well plate (Corning) with a V-shaped bottom, and centrifuged for 30 min at 4° C. and 2000 rpm. The supernatant was taken for SK-BR-3 cell of human PBMC cell binding assay. The cells and the supernatant were co-incubated at room temperature, washed twice with 1% FBS-PBS precooled on ice, and then stained for 30 min at room temperature with a PE-marked goat anti-human IgG secondary antibody (Sigma, P9170) diluted with 50 times. The stained cells were washed for three times with precooled 1% FBS-PBS, resuspended in PBS and analyzed by using a flow cytometry (FC500, Beckham) according to cell amount of one hundred thousand. A sigmoidal dose response model with variable slope of software GraphPadPrism 5 was used for analyzing. The temperature midpoint of a thermal denaturation curve was $T_{50}$.

Figure 8:
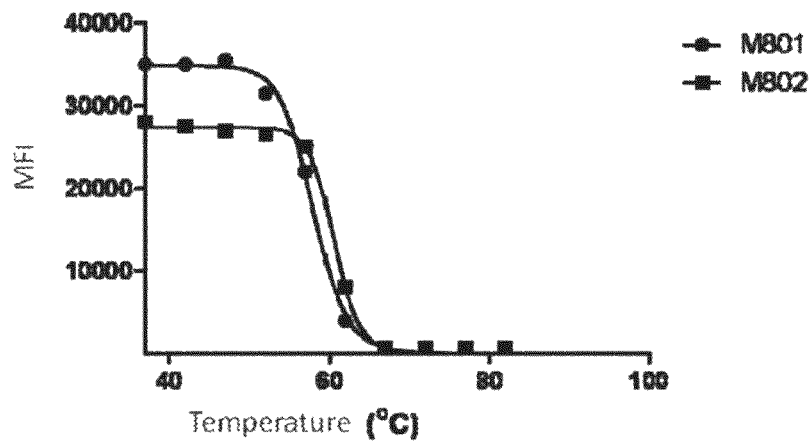
FIG. 8 is a binding condition diagram of the specific antibody to the SK-BR-3 cell after treatment via a flow cytometry detection thermal challenge experiment.
Figure 9:
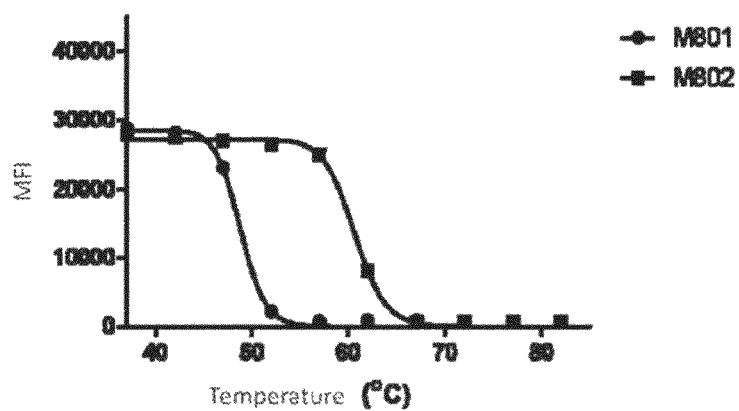
FIG. 9 is a binding condition diagram of the bispecific antibody to the human PBMC cell after treatment via the flow cytometry detection thermal challenge experiment.

The single-chain antibody fragment (ScFv) was formed by connecting a heavy chain variable region and a light chain variable region through a connecting peptide $(Gly_4Ser)_3$ (amino acids 120-134 of SEQ ID NO:5). However, it was reported that the inherent instability of ScFv possibly might affect the quality of an antibody drug (Michaelson J S, etc., Farrington G K, Lugovskoy A, Joseph I, Bailly V, Wang X, Garber E, Browing J, Glaser S M. Anti-tumor activity of stability-engineered IgG-like bispecific antibodies targeting TRAIL-R2 and LTbetaR. MAbs. 2009 March-April; 1(2):128-41.). The monovalent unit of M802 was completely consistent with that of M801, and $T_{50}$ that both of which bind to SK-BR-3 was very close (as shown in FIG. 8), for instance, the $T_{50}$ of M802 was 60.60° C. and $T_{50}$ of M801 was 57.97° C.; but, the single-chain unit of M802 used a variable region of L2K, the single-chain unit of M801 used a variable region of humanized OKT3, and $T_{50}$ that both of which bound to a T cell was great different (as shown in FIG. 9), for instance, the $T_{50}$ of M802 was 59.98° C. and $T_{50}$ of M801 was 48.79° C., and thus the thermal stability of M802 was remarkably superior to that of M801.

Example 5: Bispecific Anti-Body-Mediated in Vitro Cell-Killing Detection

1. Separation of Human Peripheral Blood Mononuclear Cells (hPBMC)

Fresh anti-freezing human blood was subject to 400 g centrifugal for 5 min and supernatant was discarded. 10-fold cell volume of red blood cell lysis buffer was added to the human blood, uniformly mixed by slightly blowing and beating, and subject to lysis at room temperature or on ice for 4-5 minutes during which appropriate shaking was needed so as to promote red blood cell lysis. 400 g centrifugal was performed for 5 min at 4□, and red supernatant was discarded. If the red cell lysis was not complete, the step 2 and step 3 were repeated once. Washing was performed for 1-2 times. 5-fold cell sedimentation volume of PBS was added, cells were resuspended to obtain sediment and subject to 400 g centrifugal for 2-3 minutes at 4□, and then supernatant was discarded. The steps were repeated once if necessary and washing was performed for 1-2 times in total. The cells were resuspended to obtain sediment with appropriate 4□ precooled PBS according to experiment demands to obtain hPBMC, and then subsequent experiments, such as counting can be performed.

2. HER2-Positive Tumor Cell-Killing Detection of Bispecific Antibody-Effectively Mediated PBMC Cells A single-cell suspension was prepared by digesting target cells (including HER2 highly-expressed SK-BR-3 breast cancer cells. HER2 highly-expressed NCI-N87 gastric cancer cells, HER2 lowly-expressed MDA-MB-231 breast cancer cells and HER2-negative HEK-293 human embryonic kidney cells, all of which were purchased from China Center for Type Culture Collection) with trypsin. The target cells were stained with CFSE with the final concentration being 5 μM, the cells were resuspended to $2\times10^5$/ml with 10% FBS-1649 cultured by these cells after staining, and cultured over night in a 90-well plate according to $2\times10^4$/well, namely 100 μl/well. According to the experiment design, 5 times of target cell count of effector cells (hPBMC) were added according to 50 μl/well, control wells were set, and the same volume of culture medium was fed into wells in which no PBMC cells need to be added. The corresponding antibody was added with 50 ul/well according to the experiment design while the PBMC cells were added, and the same volume of culture medium was fed into wells in which no antibody needs to be added. After 48 hours, the 96-well plate was taken out, cells of each well were digested with trypsin to form the single cell suspension, and correspondingly, all the supernatants and the cell suspension in this process were collected into 1.5 ml centrifuge tubes and subject to 500×g centrifugal for 5 minutes. The supernatant was discarded, and 150 μl 1% FBS-PBS was added to each well, and then cells were resuspended and uniformly mixed. PI (the final concentration of 1 μg/ml) was added for staining 10-15 min before each tube was put on an instrument for fluorescence-activated cell sorting. The proportion of CFSE and PI double positive cells, namely the death rate of target cells was detected on the instrument for fluorescence-activated cell sorting.

Figure 10:
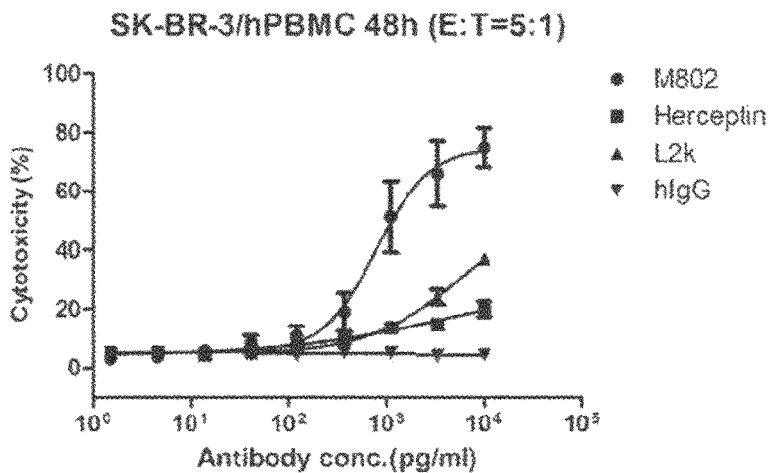
FIG. 10 is an in vitro cytotoxicity experiment result diagram of M802 and the hPBMC to the SK-BR-3 cell.
Figure 11:
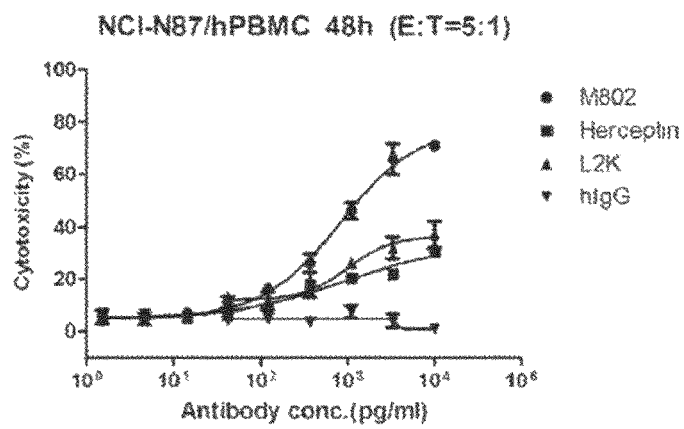
FIG. 11 is an in vitro cytotoxicity experiment result diagram of M802 and hPBMC to the NCI-N87 cell.
Figure 12:
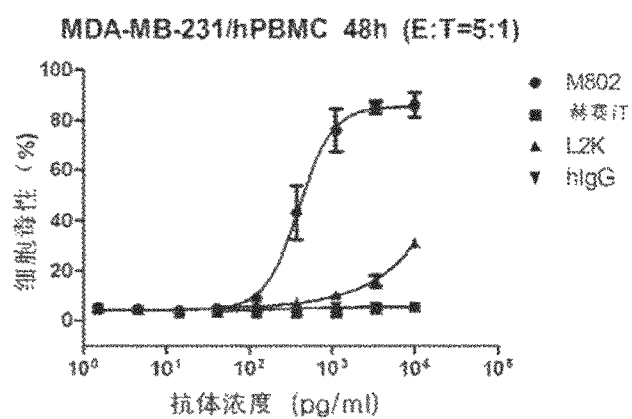
FIG. 12 is an in vitro cytotoxicity experiment result diagram of M802 and hPBMC to the MDA-MB-231 cell.
Figure 13:
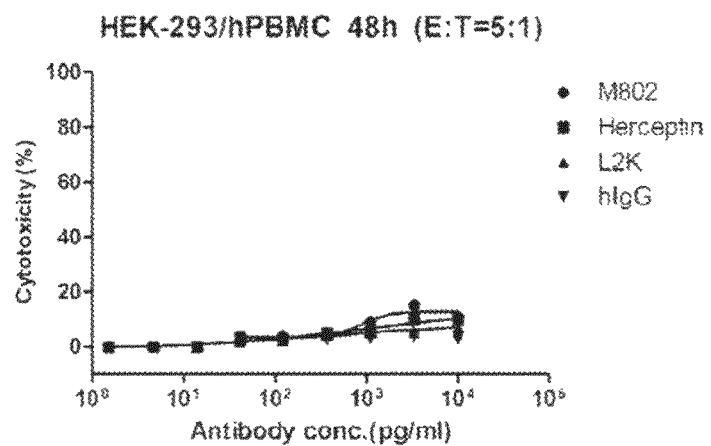
FIG. 13 is an in vitro cytotoxicity experiment result diagram of M802 and hPBMC to the HEK-293 cell.

The killing effect of M802 on HER2 highly-expressed tumor cells was very obvious, the highest killing rate reaches 80%, and the dosage of M802 was far lower than that of Herceptin® (trastuzumab) and L2K (FIGS. 10 and 11); M802 also had remarkable killing effect on HER2 lowly-expressed tumor cells, which was greatly superior to Herceptin® (trastuzumab) and L2K (FIG. 12). However, as for HER2 completely positive cells, M802 does not manifest the killing effect (FIG. 13). It was indicated that the M802 bispecific antibody had a good killing effect on tumor cells with different HER2-positive expression quantities in the presence of immune cells in an in vitro cytotoxicity experiment, but had no toxicity basically to HER2 unexpressed cells.

Example 6: Pharmacological Detection of Bispecific Antibody for Killing Subcutaneous Xenograft Tumors CIK cells were cultured according to the following steps: replenishing each portion of cells to 30 ml by using a CIK cell initiation culture solution (a serum-free X-Vivo cell culture solution +750 IU/ml IFN-γ±2% autologous plasma), adding the cells to a 75 cm² culture flask, and culturing the cells at 37 in a 5.0% $CO_2$ humidified incubator, after culture for 24 hours, adding 1 ml of CIK cell stimulation factor mixed solution (a serum-free X-Vivo cell culture solution +75 ng/ml OKT3 monoclonal antibody (homemade), 750 IU/ml interleukin 2 (IL-2) and 0.6 ng/ml interleukin 1 (IL-1α), and continuously culturing at 37□ in the 5.0% $CO_2$ humidified incubator, as concerned in the following steps, determining the matters, such as replenishing of solutions (serum-free X-Vivo cell culture solution +750 IU/ml IL-2±2% autologous plasma) and passage according to the growth situation of CIK cells to basically maintain the cells to grow at a density about $2*10^6$/ml; and finally, carrying out phenotypic detection, including CD3, CD56, CD4 and CD8, on the collected CIK cells, by using a flow cytometry FC500 and detecting the expression situations of these cell surface antigens in the CIK cells.

Tumor inoculation and CIK injection were simultaneously carried out, and $5\times10^6$ NCI-N87 tumor cells and $5>10^6$ CIK cells were injected to the right flanks of female NOD/SCID mice after being mixed. These mice were randomly grouped (8 mice/group) within two hours and then administered with M802 through tail intravenous injection with the dosages being 4 mg/kg, 2 mg/kg and 1 mg/kg. The control group was as follows: (1) the administration dosage was 4 mg/kg Herceptin® (trastuzumab); (2) the administration dosage was 4 mg/kg MC0101. The MC0101 was MSBODY as well, of which the single-chain unit was completely consistent with that of M802, and the monovalent unit variable region was the variable region of 4420 (an anti-fluorescein antibody, seeing Kranz D M, Voss E W Jr., Partial elucidation of an anti-hapten repertoire in BALB/c mice: comparative characterization of several monoclonal antifluorescyl antibodies Mol Immunol. 1981; 18(10):889-898); and (3) only was PBS injected in a negative control group. With the current day of administration as 0 day, administration was performed in the second day and the fourth day with unchanged dosage. The volumes of the tumors were measured once every three days, and the volume calculation formula was ½×length×width×width (in $mm^3$).

Figure 14:
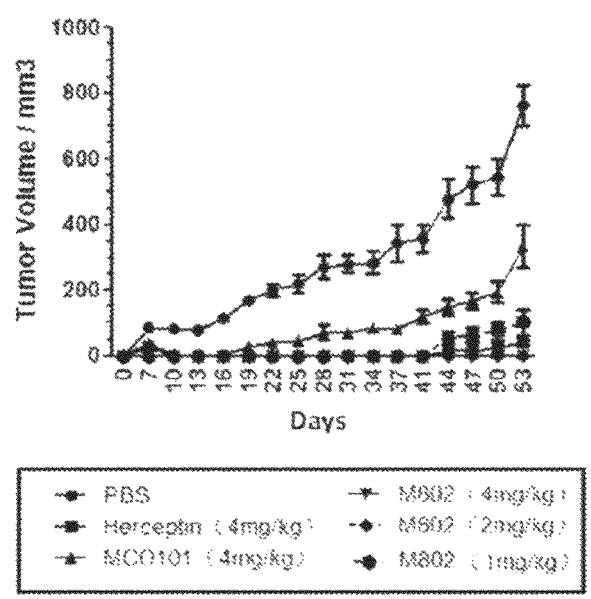
FIG. 14 is an in vitro animal experiment result diagram of M802.

In FIG. 14, both the tumor cells NCI-N87 and immune cells CIK were subcutaneously injected to female NOD/SCID mice at the same quantity; after two hours, the mice were administered through tail intravenous injection; the mice were administered once after three days and five days of administration respectively with unchanged dosage, and the tumors were measured once every three days. As shown in FIG. 14, M802 administration of different dosages shows a favorable curative effect of restricting the tumor growth, wherein tumors of all mice (16 mice in total) in 2 mg/kg and 4 mg/kg administration dosage treatment groups were completely restricted, even eliminated in the $53^{rd}$ day, whereas partial tumors of the mice in a 1 mg/kg administration dosage treatment group were also completely restricted (3/8), and the rest five mice only had smaller tumor masses (<150 mm3). In the control group, the tumors in a Herceptin® (trastuzumab) treatment group were restricted, and grew a little after 44 days; the tumors in an MC0101 treatment group were not restricted, and the volume of tumor mass reached 300 $mm^3$. The tumors in a negative group normally grew and reached about 800 $mm^3$ in the 53rd day.

It should be understood that the present invention disclosed here is not only limited to describe specific methods, solutions and matters because all of these can change. It also should be realized that terms concerned herein are only for the purpose of describing specific embodiments, but do not have an intend of limiting the scope of the present invention, and the scope of the present invention is only limited by claims attached.

Those skilled in the art should realize or confirm that many equivalents concerned in specific embodiments of the present invention in this text are used within the conventional experiment range. These equivalents are intended to come within the scope of the appended claims.

What is claimed is:

1. A bispecific antibody comprising:
    (a) a monovalent unit comprising a light chain-heavy chain pair having specificity to a human tumor cell membrane surface antigen; and
    (b) a single-chain unit comprising the amino acid sequence of SEQ ID NO: 5, wherein the single-chain unit has specificity to CD3.

2. The bispecific antibody of claim 1, wherein the light chain binds to the heavy chain through a disulfide bond and the heavy chain binds to the single-chain unit through one or more disulfide bonds.

3. The bispecific antibody of claim 1, which is a human or humanized antibody.

4. The bispecific antibody of claim 1, wherein the human tumor cell membrane surface antigen is selected from the group consisting of HER2, CD20, CD30 and CD133.

5. A method of treating a human cancer patient having a tumor cell characterized with a tumor cell membrane surface antigen comprising administering to the patient a bispecific antibody comprising (a) a monovalent unit comprising a light chain-heavy chain pair having specificity to the tumor cell membrane surface antigen; and (b) a single-chain unit comprising the amino acid sequence of SEQ ID NO: 5, wherein the single-chain unit has specificity to CD3.

6. The method of claim 5, wherein the tumor cell membrane surface antigen is selected from the group consisting of HER2, CD20, CD30 and CD133.

* * * * *

SEQUENCE LISTING

```
<160> NUMBER OF SEQ ID NOS: 18

<210> SEQ ID NO 1
<211> LENGTH: 450
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Asp Thr Thr Pro Pro Val
385                 390                 395                 400

Leu Asp Ser Asp Gly Ser Phe Phe Leu Tyr Ser Asp Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 1353
<212> TYPE: DNA
<213> ORGANISM: Homo sapiens

<400> SEQUENCE: 2
gaagtgcagc tggtggaaag cggcggcggc ctggtgcagc cgggcggatc cctgcgcctg      60
agctgcgcgg cgagcggctt taacattaaa gataccata ttcattgggt gcgccaggcg     120
ccgggcaaag gcctggaatg ggtggcgcgc atttatccga ccaacggcta tacccgctat     180
gcggatagcg tgaaaggccg ctttaccatt agcgcggata ccagcaaaaa caccgcgtat     240
ctgcagatga acagcctgcg cgcggaagat accgcggtgt attattgcag ccgctggggc     300
```

```
ggcgatggct tttatgcgat ggattattgg ggccagggca ccctggtgac cgtgagctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggaggga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgtggtgc ctggtcaaag gcttctatcc cagcgacatc   1140
gccgtggagt gggagagcaa tgggcagccg gagaacaact acgataccac gcctcccgtg   1200
ctggactccg acggctcctt cttcctctac agcgatctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                1353
```

<210> SEQ ID NO 3
<211> LENGTH: 214
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 645
<212> TYPE: DNA
<213> ORGANISM: Homo sapiens

<400> SEQUENCE: 4

```
gatattcaga tgacccagag cccgtcaagc ttaagcgcga gcgtgggcga tcgcgtgacc      60
attacctgcc gcgcgagcca ggatgtgaac accgcggtgg cgtggtatca gcagaaaccg     120
ggcaaagcgc cgaaactgct gatttatagc gcgagctttc tgtatagcgg cgtgccgagc     180
cgctttagcg gcagccgcag cggcaccgat tttaccctga ccattagcag cctgcagccg     240
gaagattttg cgacctatta ttgccagcag cattatacca ccccgccgac ctttggccag     300
ggtaccaaag tggaaattaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540
ctgagcaaag cagactacga gaaacacaaa gtctacgcct gcgaagtcac ccatcagggc     600
ctgagctcgc ccgtcacaaa gagcttcaac aggggagagt gttag                    645
```

<210> SEQ ID NO 5
<211> LENGTH: 476
<212> TYPE: PRT
<213> ORGANISM: Homo sapiens

<400> SEQUENCE: 5

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asp Ile Gln Leu Thr Gln Ser Pro Ala Ile
    130                 135                 140

Met Ser Ala Ser Pro Gly Glu Lys Val Thr Met Thr Cys Arg Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Val Ala Ser Gly Val Pro

|  |  |  | 180 |  |  |  | 185 |  |  |  | 190 |  |
|---|---|---|---|---|---|---|---|---|---|---|---|---|
| Tyr | Arg | Phe | Ser | Gly | Ser | Gly | Ser | Gly | Thr | Ser | Tyr | Ser | Leu | Thr | Ile |
|  |  |  | 195 |  |  |  | 200 |  |  |  | 205 |  |

Ser Ser Met Glu Ala Glu Asp Ala Ala Thr Tyr Tyr Cys Gln Gln Trp
210 215 220

Ser Ser Asn Pro Leu Thr Phe Gly Ala Gly Thr Lys Leu Glu Leu Lys
225 230 235 240

Gly Ala Ala Ala Glu Pro Lys Ser Cys Asp Lys Thr His Thr Cys Pro
245 250 255

Pro Cys Pro Ala Pro Glu Leu Leu Gly Gly Pro Ser Val Phe Leu Phe
260 265 270

Pro Pro Lys Pro Lys Asp Thr Leu Met Ile Ser Arg Thr Pro Glu Val
275 280 285

Thr Cys Val Val Val Asp Val Ser His Glu Asp Pro Glu Val Lys Phe
290 295 300

Asn Trp Tyr Val Asp Gly Val Glu Val His Asn Ala Lys Thr Lys Pro
305 310 315 320

Arg Glu Glu Gln Tyr Asn Ser Thr Tyr Arg Val Val Ser Val Leu Thr
325 330 335

Val Leu His Gln Asp Trp Leu Asn Gly Lys Glu Tyr Lys Cys Lys Val
340 345 350

Ser Asn Lys Ala Leu Pro Ala Pro Ile Glu Lys Thr Ile Ser Lys Ala
355 360 365

Lys Gly Gln Pro Arg Glu Pro Gln Val Tyr Thr Leu Pro Pro Ser Arg
370 375 380

Asp Glu Leu Thr Lys Asn Gln Val Ser Leu Thr Cys Arg Val Lys Gly
385 390 395 400

Phe Tyr Pro Ser Asp Ile Ala Val Glu Trp Glu Ser Asn Gly Gln Pro
405 410 415

Glu Asn Asn Tyr Lys Thr Thr Pro Pro Val Leu Lys Ser Asp Gly Ser
420 425 430

Phe Phe Leu Ala Ser Lys Leu Thr Val Asp Lys Ser Arg Trp Gln Gln
435 440 445

Gly Asn Val Phe Ser Cys Ser Val Met His Glu Ala Leu His Asn His
450 455 460

Tyr Thr Gln Lys Ser Leu Ser Leu Ser Pro Gly Lys
465 470 475

<210> SEQ ID NO 6
<211> LENGTH: 1431
<212> TYPE: DNA
<213> ORGANISM: Homo sapiens

<400> SEQUENCE: 6

| gacatcaaac | tgcagcagtc | aggggctgaa | ctggcaagac | ctggggcctc | agtgaagatg | 60 |
| tcctgcaaga | cttctggcta | cacctttact | aggtacacga | tgcactgggt | aaaacagagg | 120 |
| cctggacagg | gtctggaatg | gattggatac | attaatccta | gccgtggtta | tactaattac | 180 |
| aatcagaagt | tcaaggacaa | ggccacattg | actacagaca | aatcctccag | cacagcctac | 240 |
| atgcaactga | gcagcctgac | atctgaggac | tctgcagtct | attactgtgc | aagatattat | 300 |
| gatgatcatt | actgccttga | ctactggggc | caaggcacca | ctctcacagt | ctcctcagga | 360 |
| ggcggcggtt | caggcggagg | tggaagtggt | ggaggaggtt | ctgacattca | gctgacccag | 420 |
| tctccagcaa | tcatgtctgc | atctccaggg | gagaaggtca | ccatgacctg | cagagccagt | 480 |

-continued

```
tcaagtgtaa gttacatgaa ctggtaccag cagaagtcag gcacctcccc caaaagatgg        540
atttatgaca catccaaagt ggcttctgga gtcccttatc gcttcagtgg cagtgggtct        600
gggacctcat actctctcac aatcagcagc atggaggctg aagatgctgc cacttattac        660
tgccaacagt ggagtagtaa cccgctcacg ttcggtgctg ggaccaagct ggagctgaaa        720
ggtgcggccg cagagcccaa atcttgtgac aaaactcaca catgcccacc gtgcccagca        780
cctgaactcc tggggggacc gtcagtcttc ctcttccccc caaaacccaa ggacaccctc        840
atgatctccc ggacccctga ggtcacatgc gtggtggtgg acgtgagcca cgaagaccct        900
gaggtcaagt tcaactggta cgtggacggc gtggaggtgc ataatgccaa gacaaagccg        960
cgggaggagc agtacaacag cacgtaccgt gtggtcagcg tcctcaccgt cctgcaccag       1020
gactggctga atggcaagga gtacaagtgc aaggtctcca acaaagccct cccagccccc       1080
atcgagaaaa ccatctccaa agccaaaggg cagccccgag aaccacaggt gtacaccctg       1140
cccccatccc gggatgagct gaccaagaac caggtcagcc tgacctgccg ggtcaaaggc       1200
ttctatccca gcgacatcgc cgtggagtgg gagagcaatg ggcagccgga gaacaactac       1260
aagaccacgc ctcccgtgct ggagtccgac ggctccttct tcctcgccag caagctcacc       1320
gtggacaaga gcaggtggca gcaggggaac gtcttctcat gctccgtgat gcatgaggct       1380
ctgcacaacc actacacgca gaagagcctc tccctgtctc cgggtaaatg a               1431
```

<210> SEQ ID NO 7
<211> LENGTH: 20
<212> TYPE: PRT
<213> ORGANISM: Mus musculus

<400> SEQUENCE: 7

Met Glu Thr Asp Thr Leu Leu Leu Trp Val Leu Leu Leu Trp Val Pro
1               5                   10                  15

Gly Ser Thr Gly
            20

<210> SEQ ID NO 8
<211> LENGTH: 60
<212> TYPE: DNA
<213> ORGANISM: Mus musculus

<400> SEQUENCE: 8
atggagacag acacactcct gctatgggta ctgctgctct gggttccagg ttccactggt        60

<210> SEQ ID NO 9
<211> LENGTH: 43
<212> TYPE: DNA
<213> ORGANISM: Artificial
<220> FEATURE:
<223> OTHER INFORMATION: Synthetic Primer

<400> SEQUENCE: 9
gaggaaggat ctcgagctca agcttgatat cgccgccacc atg                          43

<210> SEQ ID NO 10
<211> LENGTH: 59
<212> TYPE: DNA
<213> ORGANISM: Artificial
<220> FEATURE:
<223> OTHER INFORMATION: Synthetic Primer

<400> SEQUENCE: 10
caattgatat cgccgccacc atggagacag acacactcct gctatgggta ctgctgctc    59

<210> SEQ ID NO 11
<211> LENGTH: 52
<212> TYPE: DNA
<213> ORGANISM: Artificial
<220> FEATURE:
<223> OTHER INFORMATION: Synthetic Primer

<400> SEQUENCE: 11
cttatcatgt ctggatcgaa gcttaattaa ctaacactct ccctgttga ag    52

<210> SEQ ID NO 12
<211> LENGTH: 43
<212> TYPE: DNA
<213> ORGANISM: Artificial
<220> FEATURE:
<223> OTHER INFORMATION: Synthetic Primer

<400> SEQUENCE: 12
cccgaggagg aacggttccg ggccgcctag ggccgccacc atg    43

<210> SEQ ID NO 13
<211> LENGTH: 59
<212> TYPE: DNA
<213> ORGANISM: Artificial
<220> FEATURE:
<223> OTHER INFORMATION: Synthetic Primer

<400> SEQUENCE: 13
caattcctag ggccgccacc atggagacag acacactcct gctatgggta ctgctgctc    59

<210> SEQ ID NO 14
<211> LENGTH: 55
<212> TYPE: DNA
<213> ORGANISM: Artificial
<220> FEATURE:
<223> OTHER INFORMATION: Synthetic Primer

<400> SEQUENCE: 14
catagagtat aatatagagt atacacctgc aggtcattta cccggagaca gggag    55

<210> SEQ ID NO 15
<211> LENGTH: 43
<212> TYPE: DNA
<213> ORGANISM: Artificial
<220> FEATURE:
<223> OTHER INFORMATION: Synthetic Primer

<400> SEQUENCE: 15
cccgaggagg aacggttccg ggccgcctag ggccgccacc atg    43

<210> SEQ ID NO 16
<211> LENGTH: 59
<212> TYPE: DNA
<213> ORGANISM: Artificial
<220> FEATURE:
<223> OTHER INFORMATION: Synthetic Primer

<400> SEQUENCE: 16
caattcctag ggccgccacc atggagacag acacactcct gctatgggta ctgctgctc    59

<210> SEQ ID NO 17
<211> LENGTH: 59
<212> TYPE: DNA
<213> ORGANISM: Artificial

```
<220> FEATURE:
<223> OTHER INFORMATION: Synthetic Primer

<400> SEQUENCE: 17
gctatgggta ctgctgctct gggttccagg ttccactggt gatatcaaac tgcagcagt        59

<210> SEQ ID NO 18
<211> LENGTH: 55
<212> TYPE: DNA
<213> ORGANISM: Artificial
<220> FEATURE:
<223> OTHER INFORMATION: Synthetic Primer

<400> SEQUENCE: 18
catagagtat aatatagagt atacacctgc aggtcattta cccggagaca gggag        55
```